(12) United States Patent
Schwitzguébel

(10) Patent No.: US 10,478,523 B2
(45) Date of Patent: Nov. 19, 2019

(54) COMPOSITION CONTAINING GLYCOSAMINOGLYCANS AND PROTEINS

(71) Applicant: ChondroNest SA, Conthey (CH)

(72) Inventor: Thierry Schwitzguébel, Villeneuve (CH)

(73) Assignee: ChondroNest SA, Conthey (CH)

( * ) Notice: Subject to any disclaimer, the term of this patent is extended or adjusted under 35 U.S.C. 154(b) by 221 days.

(21) Appl. No.: 15/509,855

(22) PCT Filed: Sep. 4, 2015

(86) PCT No.: PCT/IB2015/056740
§ 371 (c)(1),
(2) Date: Mar. 9, 2017

(87) PCT Pub. No.: WO2016/042434
PCT Pub. Date: Mar. 24, 2016

(65) Prior Publication Data
US 2017/0296698 A1    Oct. 19, 2017

(30) Foreign Application Priority Data

Sep. 18, 2014 (WO) ............... PCT/IB2014/064631
Jun. 4, 2015 (WO) ............... PCT/IB2015/054225

(51) Int. Cl.
| | | |
|---|---|---|
| *A61L 27/26* | (2006.01) | |
| *A61L 27/18* | (2006.01) | |
| *A61L 27/20* | (2006.01) | |
| *A61L 27/24* | (2006.01) | |
| *A61L 27/52* | (2006.01) | |
| *A61L 27/22* | (2006.01) | |
| *C08L 5/02* | (2006.01) | |
| *C08L 5/04* | (2006.01) | |
| *C08L 5/08* | (2006.01) | |
| *C08L 5/10* | (2006.01) | |

(52) U.S. Cl.
CPC .............. *A61L 27/26* (2013.01); *A61L 27/18* (2013.01); *A61L 27/20* (2013.01); *A61L 27/22* (2013.01); *A61L 27/24* (2013.01); *A61L 27/52* (2013.01); *A61L 2430/02* (2013.01); *A61L 2430/06* (2013.01); *A61L 2430/30* (2013.01); *A61L 2430/32* (2013.01)

(58) Field of Classification Search
None
See application file for complete search history.

(56) References Cited

U.S. PATENT DOCUMENTS

| 3,072,613 A | 1/1963 | Whelan, Jr. |
| 2010/0297066 A1* | 11/2010 | Stopek ............... A61K 9/0024 424/85.2 |

FOREIGN PATENT DOCUMENTS

| EP | 1384774 A1 | 1/2004 |
| WO | WO9719701 A2 | 6/1997 |
| WO | WO2009031047 A2 | 3/2009 |

OTHER PUBLICATIONS

Eurasian patent Office Action dated Jun. 16, 2017 and English translation for counterpart application 201790574/28.
International Search Report of PCT/IB2015/056740 dated Dec. 9, 2015.
Written Opinion of the International Search Authority dated Dec. 9, 2015.

* cited by examiner

Primary Examiner — Jeffrey T. Palenik
(74) Attorney, Agent, or Firm — Andre Roland S.A.; Nikolaus Schibli (57) ABSTRACT

A composition comprising Polyhydroxyurethanes, Glycosaminoglycans, hydrolysed glycosaminoglycans, glycosamines of glycosaminoglycans, chemically modified or not and a Protein or a peptide; said protein being collagen, elastin, keratin, fibronectin, actin, myosin, laminin, a peptide or a blend of those proteins or peptides, fibrillated, hydrolysed, chemically modified or not. This homogenous composition is obtained by the polymerisation or the covalent bounding of two preparations containing cyclic polycarbonates, polyamines, glycosaminoglycans, hydrolysed glycosaminoglycans, glycosamines, chemically modified or not and proteins or peptides or a blend of those proteins or peptides, fibrillated, hydrolysed, chemically modified or not.

24 Claims, 3 Drawing Sheets

Figure 1 - Example 1

Figure 2 - Example 2

COMPOSITION CONTAINING GLYCOSAMINOGLYCANS AND PROTEINS

CROSS-REFERENCE TO RELATED APPLICATIONS

The present application is a U.S. national stage application of PCT/IB2015/056740 filed on Sep. 4, 2015 designating the United States, and claims foreign priority to International patent application PCT/IB2015/054225 filed on Jun. 4, 2015 and International patent application PCT/IB2014/064631 filed on Sep. 18, 2014, the contents of all these three documents are herewith incorporated by reference in their entirety.

FIELD OF INVENTION

The invention generally relates to compositions containing Glycosaminoglycans, partially hydrolysed Glycosaminoglycans or Glycosamines, chemically modified or not, and proteins, partially hydrolysed proteins or peptides, chemically modified or not, such as for example collagens.

STATE OF THE ART

The formulation of homogenous compositions containing highly hydrophilic Glycosaminoglycans, partially hydrolysed Glycosaminoglycans or Glycosamines, chemically modified or not, and proteins, partially hydrolysed proteins or peptides, chemically modified or not provides viscoelastic solids or semi-solids with limited mechanical properties and limited properties for biological, pharmacological or medicinal usages.

GENERAL DESCRIPTION OF THE INVENTION

The problems mentioned in the previous chapter may be solved with the composition according to the present invention.

To this effect, the composition according to the invention comprise a polyhydroxyurethane, a glycosaminoglycan, a partially hydrolysed Glycosaminoglycans or Glycosamines, chemically modified or not, and proteins, partially hydrolysed proteins or peptides, chemically modified or not. The polyhydroxyurethane is obtained by the covalent coupling of cyclic carbonates (CC) and polyamines (PA) chemical functions.

Preferably the composition is obtained by the polymerisation or covalent bound formation of a preparation containing molecules with cyclic polycarbonates functional groups and Glycosaminoglycans, partially hydrolysed Glycosaminoglycans or Glycosamines, or chemically modified or not with a preparation containing molecules with polyamines functional groups, proteins, partially hydrolysed proteins or peptides, chemically modified or not. The Glycosaminoglycans, partially hydrolysed Glycosaminoglycans or Glycosamines and the proteins, partially hydrolysed or not, or the peptides may be chemically modified with the constituents of the polyhydroxyurethanes.

The Glycosaminoglycans partially hydrolysed Glycosaminoglycans or Glycosamines chemically modified with monomers or pre-polymers of the polyhydroxyurethanes can be covalently bound to proteins, partially hydrolysed proteins or peptides, chemically modified or not with monomers or pre-polymers of the polyhydroxyurethanes to give new compositions with innovative physical, biological, pharmacological or medicinal properties.

The composition according to the invention may be used in several applications such as the preparation of micro-gel or micro-particles to deliver active pharmaceutical substances or to support living cells, or for the treatment of surfaces in contact with living materials, or for the treatment of surfaces to provide them specific affinities to polysaccharides, proteins, partially hydrolysed proteins and peptides, or to chemically modify proteins, partially hydrolysed proteins and peptides to provide them novel physical, biological, pharmacological or medicinal properties or the reconstruction and the substitution of extra cellular matrix in vitro or in vivo.

The extra cellular matrix is the non cellular part presents in all tissues and organs. Its functions are essentially linked to its structure and its physical properties, but also to its biochemical composition and its essential constituents and their biomechanical functions.

Fundamentally the Extra cellular Matrix (ECM) is constituted of water, proteins and polysaccharides. Every ECM processes a unique biochemical composition having in common the essential presence of proteins exhibiting various conformations such as the fibrillar structure of collagens, and glycosaminoglycans forming hydrated gels. Collagens and the other fibrillar proteins are essentially hydrophobic in the haemostatics' conditions of the ECM, while glycosaminoglycans are strongly hydrophilic. The reconstruction in vitro and in vivo of an ECM, based on those two essential families of substances, with the appropriate mechanical characteristics in biocompatible conditions is one of the applications of this innovative formulation.

When the ECM is damaged or destroyed due to different affections or traumas, or when it has been deformed, or has partially or totally disappeared due to processes associated with aging, traumas, or erosion, techniques currently exist to reconstruct or replace it.

Those techniques can be classified in three general families:
- The use of implants and biocompatible prostheses with no relation to the original composition of the ECM and without living cells.
- The use of implants and biocompatible mechanical scaffolds based on compositions with limited relation to the original composition of the ECM, but allowing living cells to proliferate in the mimetic ECM.
- Autologous grafts based on the extraction of healthy and functional ECM of the patient to reconstruct the damaged parts.

Those techniques are widely used but they all carry their well knows own drawbacks, such as:
- The heavy operation traumas and the difficulties to replace prostheses without living cells.
- The weak integration and incorporation of functionalised scaffolds with neighbouring ECM.
- The limitation to find adequate healthy ECM in autologous grafts.

The present invention allows reconstructing a biocompatible ECM constituted of polyhydroxyurethanes and the essential constituents of the original ECM, the proteins and the glycosaminoglycans. This ECM is formed in vitro or in vivo by the polymerisation of the monomers or pre-polymers functional groups of the polyhydroxyurethanes supporting the solubilisation and the creation of close contacts or covalent bonds between proteins, partially hydrolysed proteins or peptides, chemically modified or not and Glycosaminoglycans, partially hydrolysed Glycosaminoglycans or Glycosamines chemically modified or not in biocompatible conditions.

In some embodiments the composition according to the invention is obtained via two preparations, named "preparation a" and "preparation b" in the present document.

Preparation a

The essential constituents for its intended use in the preparation a are the glycosaminoglycans such as, the Chondroitin sulphates; the Hyaluronic acid; the Heparan sulphates; the Dermatan sulphates; the Keratan sulphates; the Aggrecan; their hydrolysed fractions or their glycosamines and polyglycosamines constituents; the above constituents can be chemically modified with one or more of the monomers or pre-polymers unit of the polyhydroxyurethane and the mixtures of those substances, here down named the "GAG blend".

The "GAG blend" of the preparation a is dispersed or dissolved in the continuous media containing an acceptable solvent at a concentration above 1% and optionally monomers or pre-polymers of the polyhydroxyurethane not covalently bound to the "GAG blend", for example a cyclic polycarbonates with cycles of 5 to 8 atoms.

More particularly cyclic polycarbonates of polyhydroxylated molecules carrying at least three, primary or secondary, non aromatic, hydroxyl functions.

For example, cyclic polycarbonates of erythritol, xylitol, arabitol, ribitol, sorbitol, dulcitol, mannitol, maltitol, isomaltitol, lactitol, or polyether polyols and the mixtures of the above as well as cyclic carbonates and polycarbonates of (1,2-dihydroxyethyl), or (2,3-dihydroxypropyl) ether, ester, ketone, amide, phosphate, sulphate, sulphide, disulfide, alkanes, cycloalkanes, alkenes, cycloalkenes, aryls and heterocycles containing one or more oxygen atom, or aromatic heterocycles containing one or more nitrogen or sulphur atom.

The non commercial cyclic polycarbonates of the preparation a are obtained following methods described in the literature and the prior art, for example, the method described by Union Carbide Corporation in the U.S. Pat. No. 3,072,613 dated 8 Jan. 1963.

For example the non commercial monomer cyclic polycarbonate of Diglycerol is obtained by slow heating up to a temperature of 130° Celsius a mixture containing Diglycerol, an excess of diethyl carbonate and a catalytic quantity of sodium carbonate. The yield is very high.

The pre-polymers of the polyhydroxyurethanes with a Degree of polymerisation from 3 to 200,000, preferably from 3 to 20,000 are obtained following methods described in the literature and the prior art, for example, the method described by Union Carbide Corporation in the U.S. Pat. No. 3,072,613 dated 8 Jan. 1963. The pre-polymer of the polyhydroxyurethanes of the preparation a are formulated and prepared by ways ensuring that their terminal endings are cyclic carbonate functions.

The chemically modified glycosaminoglycans with components of the polyhydroxyurethane are obtained following methods described in the literature and the prior art. For example, a modified Hyaluronic acid of the "GAG blend" is obtained by its deacetylation in caustic media, followed by its esterification with the cyclic polycarbonate of Diglycerol, followed by its carbamatation with the same or another cyclic polycarbonate after pH adjustment between 8 and 5. The glycosaminoglycan chemically modified with any one of the polycarbonates described above can be further modified with a diamine or polyamine described in the present invention. The reaction of carbamatation of the side chain of the modified Hyaluronic acid is carried in the presence of an acceptable solvent, such as for example, but not limited to water at a temperature between zero and 150° Celsius, preferably between 15 and 80° Celsius. The resulting chemically modified Hyaluronic acid can be further carbamated with a cyclic polycarbonate in the condition described above. The successive carbamatation of the modified Hyaluronic acid can be further made to construct a Polyhydroxyurethane side chain on the modified Hyaluronic acid of 3 to 25 monomer entities terminated with cyclic carbonates. The same procedure can be applied to partially hydrolysed Glycosaminoglycans or Glycosamines described in the invention.

Additionally the preparation a can contain proteins, partially hydrolysed proteins or peptides, the "Blend of Proteins", chemically modified with pre-polymers of polyhydroxyurethanes or polyhydroxyurethanes, terminated with cyclic carbonates functions.

The chemically modified "Blend of Proteins" is obtained, for example by dissolving collagen in Bis(1,4-aminopropyl) Piperazine, followed by its amidation with a mixture of Carbodiimide (EDC) and N-Hydroxysuccinimide, followed by the precipitation of the modified collagen in TBME (Ter-ButylMethyl Ether), followed by the dissolution and neutralisation of the wet precipitate in a solution of anhydrous Ethanol with 4% of acetic acid, followed by a precipitation of the modified collagen in Ethyl acetate, centrifugation and drying under vacuum. Similarly to the chemical modification of the "GAG Blend" described above, this chemically modified "Blend of Proteins" can, after its amidation, be further carbamated with one of the cyclic polycarbonate described in the present invention in the presence of an acceptable solvent at a temperature between zero and 150° Celsius, preferably between 15 and 80° Celsius. The resulting chemically modified protein can be further carbamated with one of the diamine or polyamine described in the present invention. The successive carbamatation of the "Blend of Proteins" can be further made to construct a Polyhydroxyurethane side chain of 2 to 26 monomers entities terminated by cyclic carbonates functions on the "Blend of Proteins".

The preparation a contains the constituents of the invention carrying terminal non reacted cyclic carbonates. The quantity of non reacted cyclic carbonates functions from all constituents of the preparation a is sufficient to polymerise or covalently bind to the non reacted primary or secondary amine functions from all constituents of the preparation b to obtain the desired properties from the composition containing polyhydroxyurethanes and glycosaminoglycans, partially hydrolysed Glycosaminoglycans or Glycosamines, chemically modified or not and proteins, partially hydrolysed proteins or peptides, chemically modified or not.

Preparation b

The essential constituents for the intended use in the preparation b are the proteins, such as, the collagens, the elastins, the keratins, the fibronectins, the actins, the myosins, the laminins, their hydrolysed fractions or peptides; the above constituents chemically modified with one or more components of the polyhydroxyurethanes and the mixtures of those substances, hereafter named the "Blend of Proteins".

The chemically modified, proteins or peptides with components of the polyhydroxyurethane are obtained following methods described in the literature and the prior art. For example, a modified collagen for the "Blend of Proteins" is obtain by dissolving collagen in Bis(1,4-aminopropyl) Piperazine, followed by the amidation with a mixture of Carbodiimide (EDC) and N-Hydroxysuccinimide, followed by the precipitation of the modified collagen in TBME (Ter-ButylMethyl Ether), followed by the dissolution and neutralisation of the wet precipitate in a solution of anhydrous Ethanol with 4% of acetic acid, followed by a precipitation of the modified collagen in Ethyl acetate, centrifugation and drying under vacuum. Similarly to the chemical modification of "The GAG Blend" described in the preparation a, the chemically modified protein or peptide can, after its amidation, be further carbamated with one of the cyclic polycarbonate described in the present invention in the presence of an acceptable solvent at a temperature between zero and 150° Celsius, preferably between 15 and 80° Celsius. The resulting chemically modified protein can be further carbamated with one of the diamine described in the present invention. The successive carbamatation of the "Blend of Proteins" can be further proceed to construct a Polyhydroxyurethane side chain of 1 to 25 monomers entities terminated by primary and secondary amine functions on the "Blend of Proteins".

The "Blend of Proteins" is dispersed or dissolved in the continuous media of the preparation b containing an acceptable solvent such as for example, but not limited to water, at a concentration above 1% and optionally monomers or pre-polymers of the polyhydroxyurethane not covalently bound to the "Blend of Proteins", for example a primary or secondary polyamines.

The useful primary or secondary polyamines in the present invention are primary or secondary polyamines of ether, ester, ketone, amide, phosphate, sulphate, sulphide, disulfide, alkanes, cycloalkanes, alkenes, cycloalkenes, aryls, substituted or not with hydroxyl functions; or primary or secondary polyamines and primary or secondary polyalkylamines of heterocycles containing one or more oxygen, nitrogen or sulphur atom; or polyetheramines simple or mixed of ethylene glycol and propylene glycol; or a mixture of those compounds.

The pre-polymers of the polyhydroxyurethanes with a Degree of polymerisation from 3 to 200,000, preferably from 3 to 20,000 are obtained following methods described in the literature and the prior art, for example, the method described by Union Carbide Corporation in the U.S. Pat. No. 3,072,613 dated 8 Jan. 1963. The pre-polymer of the polyhydroxyurethanes of the preparation b are formulated and prepared by ways ensuring that their terminal endings are primary or secondary amine functions. Additionally the preparation a can contain Glycosaminoglycans, partially hydrolysed Glycosaminoglycans or Glycosamines, the "GAG Blend", chemically modified with pre-polymers of polyhydroxyurethanes or polyhydroxyurethanes, terminated with primary or secondary amine functions.

Additionally the preparation a can contain Glycosaminoglycans, partially hydrolysed Glycosaminoglycans or Glycosamines, the "GAG Blend", chemically modified with monomers or pre-polymers of polyhydroxyurethanes or polyhydroxyurethanes, terminated with primary or secondary amine functions alternatively obtained by amidation. For example, a modified Chondroitin sulphate of the "GAG blend" is obtained by amidation with a diamine or polyamine, such as, but not limited to 1,3-diamino, 2-propanol catalysed by a carbodiimide (EDC) and N-Hydroxysuccinimide at room temperature. The degree of amidation is controlled by the catalyst amount. A partially or fully amidated Chondroitin sulphate obtained is purified by successive washing, precipitation and re-suspension in polar and less polar solvents. The partially amidated Chondroitin sulphate can be further amidated with pre-polymers of polyhydroxyurethanes or polyhydroxyurethanes, terminated with primary or secondary amine functions. The reaction is carried at temperature between zero and 80° Celsius, preferably, 20 and 60° Celsius with carbodiimide and N-Hydroxysuccinimide catalyst system. The modified glycosaminoglycan is isolated by successive washing, precipitation and re-suspension in polar and less polar solvents.

The preparation b contains the constituents of the invention carrying terminal non reacted primary or secondary amine functions from the di and polyamines. The quantity of non reacted primary or secondary amine functions from the di and polyamines from all constituents of the preparation b is sufficient to polymerise or covalently bind to the non reacted cyclic carbonate functions from all constituents of the preparation a to obtain the desired functions from the composition containing polyhydroxyurethanes and glycosaminoglycans, partially hydrolysed Glycosaminoglycans or Glycosamines, chemically modified or not and proteins, partially hydrolysed proteins or peptides, chemically modified or not.

Composition from Preparations a and b

The blend of the preparations a and b allows the creation of a homogenous composition containing the constituents of the present invention, namely the "GAG blend", the "Blend of Proteins" in combination with polyhydroxyurethanes or covalently bound with polyhydroxyurethanes.

The useful proportions of the preparations a and b for the blended composition are linked to the desired final application. The molar ratio of cyclic carbonates to amine functions is set between 0.02 and 50. In the example of the substitution or reconstruction of the ECM, those proportions are calculated such as the number of cyclic carbonate functions coming from the preparation a or b are equal or slightly higher than the number of primary and secondary amine functions coming from the preparation b or a.

The cyclic carbonate functions from the preparation a or b react with the primary and secondary amine functions from the preparation b or a by polymerisation or covalent bounds to form various Polyhydroxyurethanes. During this mixing of the two preparations, the temperature may increase to temperature between 15 and 150° Celsius depending on the constituents of phase a and b, their concentration and the type of mixing technology chosen from the known technologies. The polymerisation or covalent bounds to form various Polyhydroxyurethanes can additionally be controlled by catalysts such as, but not limited to Zinc, Magnesium, Bismuth, Aluminium salts or covalent compounds or Infra Red photonic sources to control the speed of polymerisation and covalent bounds formation.

The obtained composition comprising Polyhydroxyurethanes, Glycosaminoglycans and proteins is for example useful for the preparation of micro-gel or micro-particles to deliver active pharmaceutical substances or to support living cells, or for the treatment of surfaces in contact with living materials, or for the treatment of surfaces to provide them specific affinities to polysaccharides, proteins, partially hydrolysed proteins and peptides, or to chemically modify proteins and partially hydrolysed proteins and peptides to provide them novel physical, biological, pharmacological or medicinal properties or for the reconstruction and the substitution of extra cellular matrix in vitro or in vivo.

The innovative composition obtained by the mixture of the preparations a and b can be complemented by physiological solution, cells and their growth factors regulators, minerals, particularly phosphate salts and any other component normally present in the ECM environment or for the purpose of the application.

This innovative composition is for example useful for the substitution and the reconstruction of connective, epithelial, nervous, muscular, bones, cartilaginous, or dermal, animal or human extra cellular matrix.

This innovative composition is also useful to coat the surfaces of foreign materials implanted in living organisms for permanent or transitory periods.

DETAILED DESCRIPTION OF THE INVENTION

The invention will be better understood in the present chapter, with some examples and the following figures.

EXAMPLE 1

Preparation a

In a reactor fitted with a mechanical agitator we add 20 parts of Triglycerol (Polyglycerol-3; Solvay), 50 parts of diethyl carbonate and 0.5 part of sodium carbonate finely grounded.

The blend under agitation is heated over a period of one hour to 90° Celsius, until the mixture appears homogenous. It is than slowly heated to 130° Celsius in one to two hours and then kept at the temperature for another one to two hours. The ethyl alcohol formed during the reaction is eliminated by distillation. After three hours, the mixture is placed under vacuum of about 15 mbar to remove residues of ethyl alcohol and diethyl carbonate.

The mixture is hot filtered to remove the catalyst and 1.5 parts of Chondroitin-4-sulphate sodium salt (Sigma-Aldrich) is added.

Preparation b

We add 1.5 part of chemically hydrolysed collagen type II of porcine origin (Meitek Technology Qingdao Co. Ltd) to 20 parts of 1,3-diamino-2-propanol. The preparation b is kept under agitation at room temperature to obtain a viscous homogenous liquid.

Composition from the Preparations a and b 20 parts of preparation a are preheated at about 50° Celsius. 6.5 parts of preparation b are added and blended with a conventional high shear mixing equipment. The temperature of the composition rises rapidly to 80° Celsius. The composition is cooled down to around 45° Celsius and 4.8 parts of a 5% Hyaluronic acid (Sigma-Aldrich) solution in a PBS buffer is added and mixed with the same equipment as above.

Figure 1:
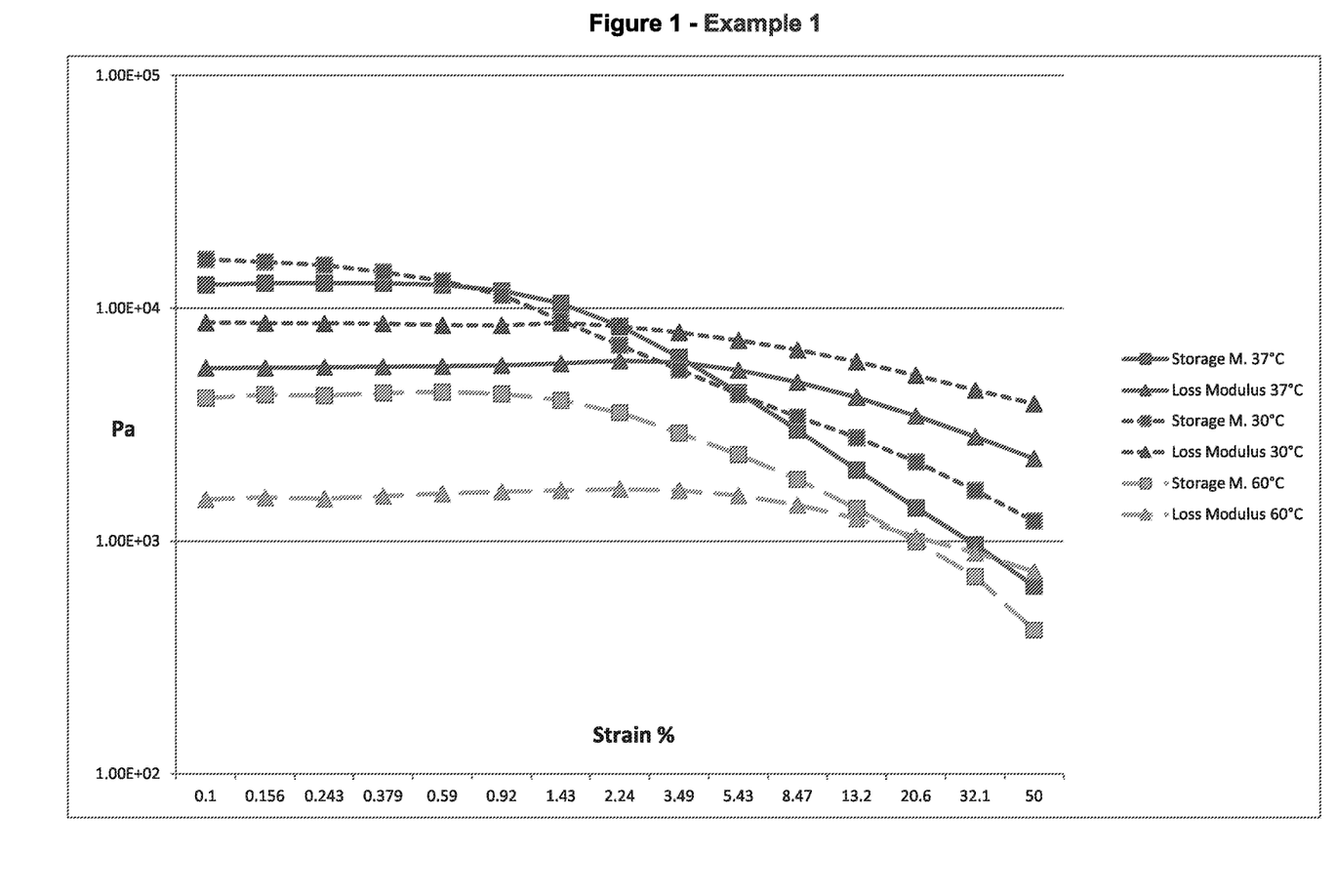
FIG. 1 shows the viscoelastic rheological properties of a composition according to a first example of the invention.

The composition obtained is useful as a substitute of Extra Cellular Matrix, and shows viscoelastic rheological properties as shown in the FIG. 1.

EXAMPLE 2

Preparation a

In a reactor fitted with a mechanical agitator we add 20 parts of Triglycerol (Polyglycerol-3; Solvay), 12 parts of Sorbitol (Sigma-Aldrich), 100 parts of diethyl carbonate and 1 part of sodium carbonate finely grounded.

The blend under agitation is heated over a period of one hour to 115° Celsius, until the mixture appears homogeneous. It is than slowly heated to 130° Celsius in about one hour and then kept at the temperature for another one to two hours. The ethyl alcohol formed during the reaction is eliminated by distillation. After three hours, the mixture is placed under vacuum of about 15 mbar to remove residues of ethyl alcohol and diethyl carbonate.

The mixture is hot filtered to remove the catalyst and 3.2 parts of Chondroitin-4-sulphate sodium salt (Sigma-Aldrich) are added.

Preparation b

We dissolve 0.7 part of insoluble Type I collagen from beef Achilles tendon (Sigma-Aldrich) in 7 parts of 1,3-diamino-2-propanol, 4.9 parts of 3,6-dioxaoctamethylendiamine (JEFFAMIN EDR 148, Huntsman), and 2.1 parts of Hexamethylenediamine. We add 2.1 parts of chemically hydrolysed collagen type II of porcine origin (Meitek Technology Qingdao Co. Ltd) at the mixture preheated at about 40° Celsius to obtain the preparation b.

Figure 2:
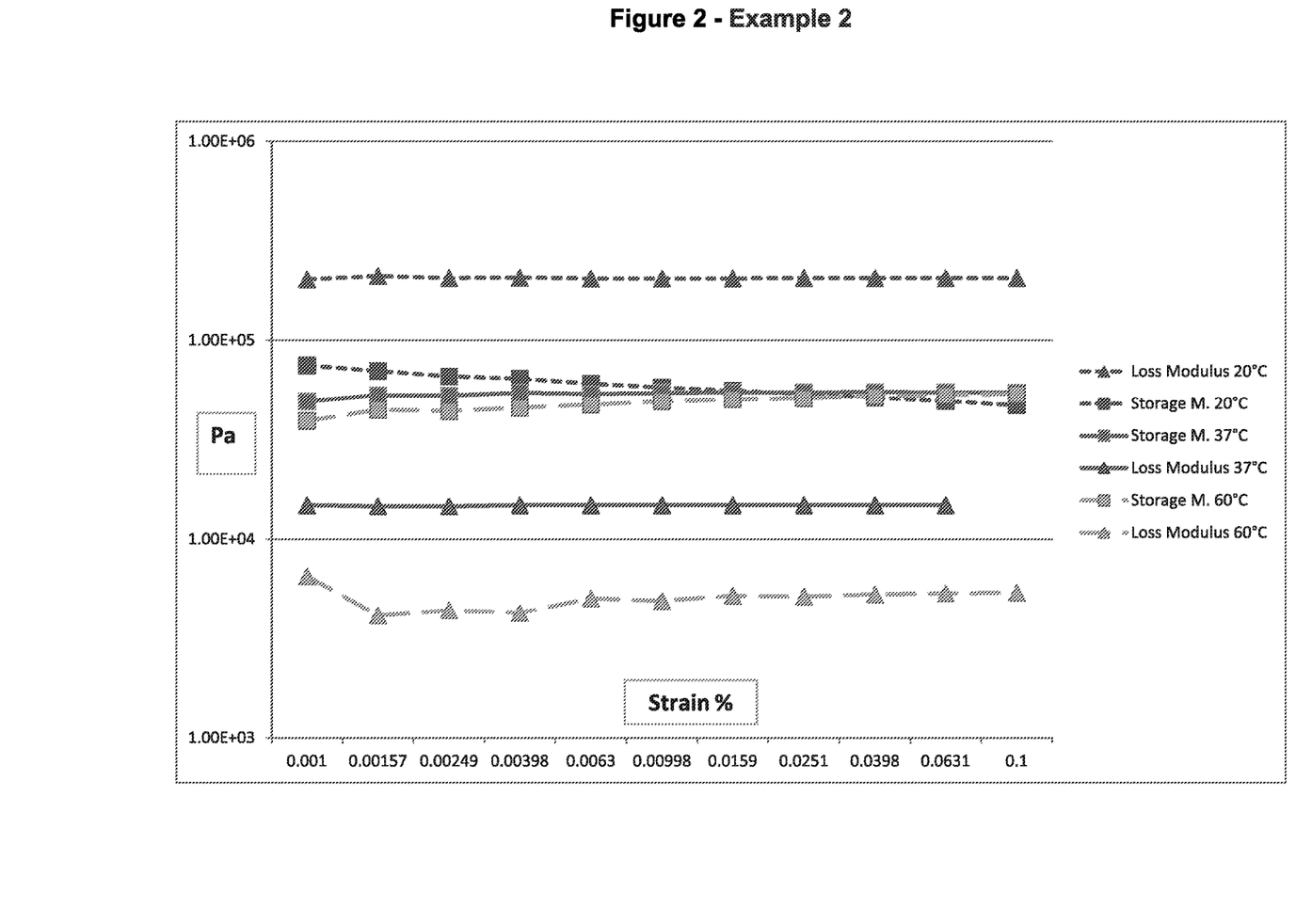
FIG. 2 shows the viscoelastic rheological properties of a composition according to a second example of the invention.

Composition from the Preparations a and b 20 parts of preparation a are preheated at about 50° Celsius. 15.8 parts of preparation b are added and blended with a conventional high shear mixing equipment. The temperature of the composition rises rapidly above 80° Celsius. The obtained composition is useful for example to coat surfaces of foreign materials implanted in living organisms for permanent or transitory periods. The composition 2 shows viscoelastic rheological properties as shown in the FIG. 2.

EXAMPLE 3

Preparation a

In a reactor fitted with a mechanical agitator we add 23.3 parts of Triglycerol (Polyglycerol-3; Solvay), 6.7 parts of Diglycerol (TCI Europe N.V), 75 parts of diethyl carbonate and 1.5 part of sodium carbonate finely grounded. The blend under agitation is heated over a period of one hour to 90° Celsius, until the mixture appears homogeneous. It is than slowly heated to 130° Celsius in about one hour and then kept at the temperature for another one to two hours. The ethyl alcohol formed during the reaction is eliminated by distillation. After three hours, the mixture is placed under vacuum of about 15 mbar to remove residues of ethyl alcohol and diethyl carbonate. The mixture is hot filtered to remove the catalyst and 2 parts of Chondroitin-4-sulphate sodium salt (Sigma-Aldrich) are added.

Preparation b

We dissolve 1 part of insoluble Type I collagen from beef Achilles tendon (Sigma-Aldrich) in 10 parts of 1,3-diamino-2-propanol. We add 1 parts of chemically hydrolysed collagen type II of porcine origin (Meitek Technology Qingdao Co. Ltd) at the mixture preheated at about 50° Celsius to obtain the preparation b.

Figure 3:
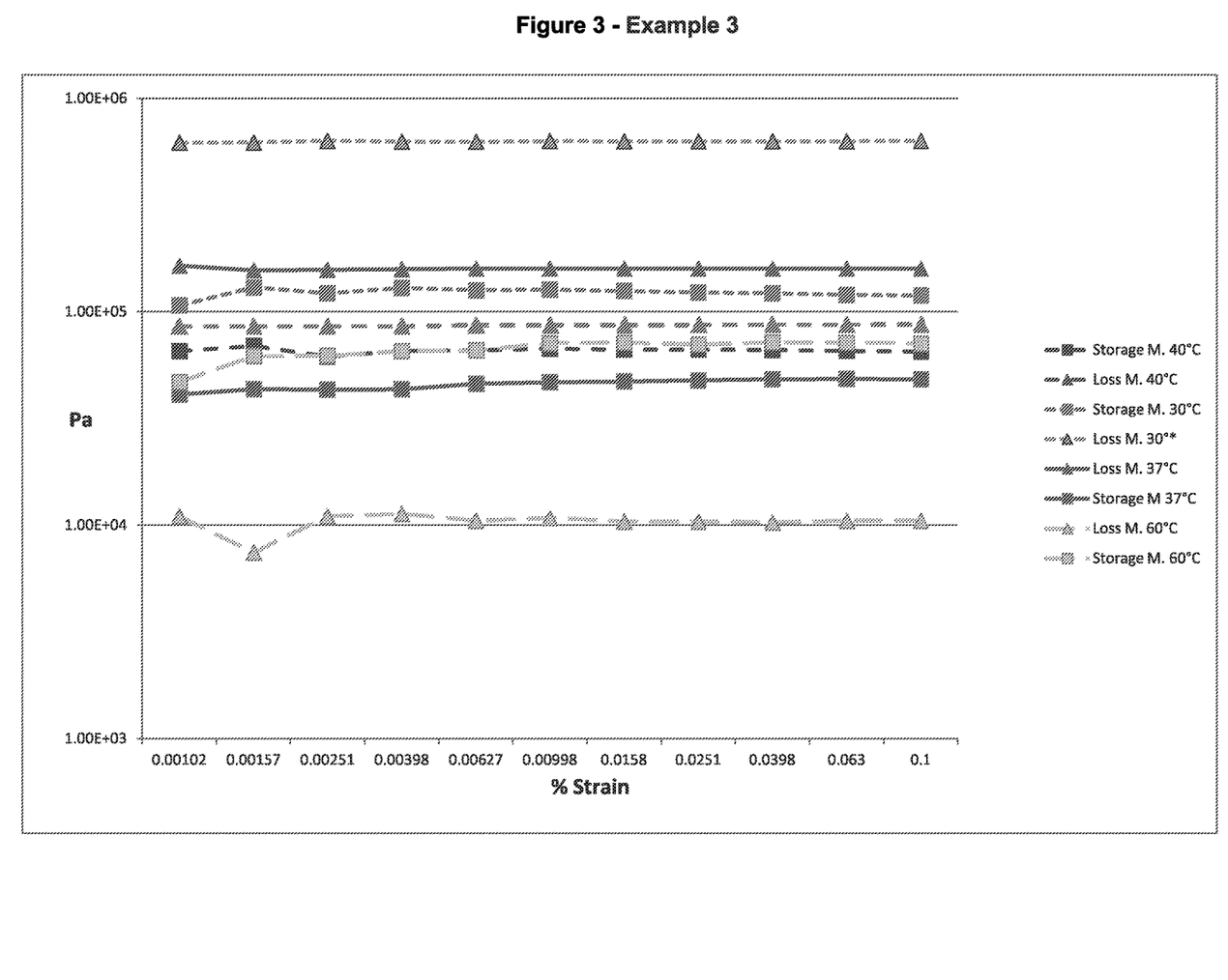
FIG. 3 shows the viscoelastic rheological properties of a composition according to a third example of the invention.

Composition from the Preparations a and b 15 parts of preparation a are preheated at about 50° Celsius. 7.25 parts of preparation b are added and blended with a conventional high shear mixing equipment. The temperature of the composition rises rapidly above 80° Celsius. The obtained composition is useful for example as substitute of the extra cellular matrix, or to coat surfaces of foreign materials implanted in living organisms for permanent or transitory periods. The composition 3 shows viscoelastic rheological properties as shown in the FIG. 3.

EXAMPLE 4

Preparation a

In water with 0.25 M NaOH we introduce 5% by weight of Hyaluronic Acid (Sigma-Aldrich), the product is deacetylated at Room temperature for 12 H. We add Diglycerol Dicarbonate prepared as described above in 50% acetone solution to the mixture. The quantity added is calculated as the amount of free carboxylic acid of the Hyaluronic acid. After 1 to 12 hours at a temperature between 20° and 75° Celsius, the reaction media is neutralised with 1 M aqueous HCl leading to the exhaust of $CO_2$. We add to the composition the same amount of Diglycerol Dicarbonate in 50% acetone as previously at a temperature between 20° and 75° Celsius. The mixture is stirred for 10 minutes to 10 hours and concentrated under vacuum to provide a chemically modified glycosaminoglycan.

Preparation b

In Ethyl Acetate we add 5% by weight of 1,4-Bis(3-aminopropyl)piperazine and 6% by weight of cyclic diglycerol dicarbonate. The reaction media is heated between 50 and the boiling point for 2 to 15 hours to produce the corresponding polyhydroxyurethane terminated by amine functions. The Ethyl Acetate is removed by vacuum distillation and the polyhydroxyurethane re-dissolved in an acceptable solvent such as for example, but not limited to water. We add 1% of chemically hydrolysed collagen type II of porcine origin (Meitek Technology Qingdao Co. Ltd) to the pre-polymer of polyhydroxyurethane.

Blend of a and b

Preparation a and b are mixed in proportions to ensure that the cyclic carbonate functions are equal to or slightly above the amine functions. The resulting composition is a solid transparent product.

EXAMPLE 5

Preparation b

We add to 400 ml of 1,4-Bis(3-aminopropyl) piperazine 10 g of chemically hydrolysed collagen type II of porcine origin (Meitek Technology Qingdao Co. Ltd). The mixture is stirred at room temperature until dissolution. We further add 17.5 g of N-Hydroxysuccinimide and 26.75 g of carbodiimide (EDC) in small portion and stir for 12 hours at room temperature to amidate the protein.

The amidated protein is precipitated from the reaction mixture with two times its volume of ter-Butyl Methyl Ether (TBME).

The 90 ml wet precipitate from the TBME phase is neutralised with six time its volume of anhydrous EtOH/ Acetic acid 4%. The re-dissolved amidated collagen in neutralised organic solution is precipitated with 2.5 times its volume of Ethyl Acetate, centrifuged and dried under vacuum.

Blend of Preparation a from Example 4 and Preparation b

Preparation a from example 4 and b are mixed in proportions to ensure that the cyclic carbonate functions are equal to or slightly above the amine functions. The resulting composition is a viscoelastic transparent product.

EXAMPLE 6

Preparation b

We take 10 parts of preparation b from Example 5 (the "Blend of Proteins") which is a modified protein, 5 parts of preparation b from example 4 which is a polyhydroxyurethane pre-polymer terminated with amine functions and collagen with and 35 parts of preparation b from Example 3. This pre-blend is the composition containing the amine functions.

Preparation a

To 20 parts of the preparation a from Example 4 (The "GAG Blend") which is a modified Glycosaminoglycan, we add and dissolve at a temperature between 45 and 65° Celsius 15 parts of bis-(cyclic carbonate) of Triglycerol prepared as described in example 1. This provide a composition with the cyclic carbonate functions.

Blend of a and b

Those two pre-blends are mixed to give a composition containing polyhydroxyurethane, modified Glycosaminoglycans, proteins and modified proteins, resulting in an elastic semi-solid white foam.

EXAMPLE 7

Preparation a

Preparation a from example 4

Preparation b

We dissolve 0.7 part of insoluble Type I collagen from beef Achilles tendon (Sigma-Aldrich) in 7 parts of 1,3-diamino-2-propanol, 4.9 parts of 3,6-dioxaoctamethylendiamine (JEFFAMIN EDR 148, Huntsman), and 2.1 parts of Hexamethylenediamine. We add 2.1 parts of chemically hydrolysed collagen type II of porcine origin (Meitek Technology Qingdao Co. Ltd) to the mixture preheated at about 40° Celsius to obtain the preparation b.

We add to 10 parts of this preparation b of collagen in monomer of polyhydroxyurethanes, 5 parts of pre-polymer of polyhydroxyurethanes terminated with amine functions as prepared in the preparation b of the example 4.

Blend of a and b

To those 15 parts of preparation b which contain the amine functions we add and mix 20 parts of preparation a from example 4 to give a transparent hydrogel at 37° Celsius with polyhydroxyurethanes, chemically modified glycosaminoglycans and proteins.

The invention claimed is:

1. A composition comprising a first, second and third constituents, wherein
   the first constituent is a glycosaminoglycan, a hydrolyzed glycosaminoglycan, a glycosamine, chemically modified or not or a blend of different glycosaminoglycans, hydrolysed glycosaminoglycans, glycosamines, chemically modified or not;
   the second constituent is a protein, a peptide or a blend of different proteins or peptides; and
   the third constituent is a polyhydroxyurethane (PHU) which is obtained by the covalent coupling of bis or poly cyclic carbonates (CC) and di or polyamines (PA) molecules,
   the composition further carbamated successively with CC and PA to obtain CC or PA terminated PHU chemically grafted on glycosaminoglycans, hydrolysed glycosaminoglycans, glycosamines of glycosaminoglycans or the blend of the different glycosaminoglycans, hydrolysed glycosaminoglycans, glycosamines of glycosaminoglycans.

2. The composition of claim 1, wherein the protein is a collagen, elastin, keratin, fibronectin, actin, myosin, laminin, a peptide or a blend of those proteins or peptides, hydrolyzed, chemically modified, fibrillated or not.

3. The composition of claim 1, obtained by polymerization or covalent bound formation between the constituents of two preparations a and b, wherein the preparation a has at least 1% of glycosaminoglycans, hydrolysed glycosaminoglycans, glycosamines, or chemically modified glycosaminoglycan, hydrolyzed glycosaminoglycans, glycosamines with cyclic polycarbonates or with Pre-polymer of polyhydroxyurethanes terminated by cyclic carbonates functions (PRE-CC) or a blend of those different constituents in a blend containing acceptable solvents and optionally CC monomers of PHU or PRE-CC or a blend of PRE-CC and CC to ensure that the preparation a contains cyclic carbonate functions, and the preparation b has at least 1% of collagens, elastins, keratins, fibronectins, actins, myosins, laminins, peptides, hydrolysed, fibrillated or not, or chemically modified collagens, elastins, keratins, fibronectins, actins, myosins, laminins, peptides, hydrolyzed, fibrillated or not with PA or with Pre-polymer of polyhydroxyurethanes terminated by amines functions (PRE-PA) or a blend of those constituents in a blend containing acceptable solvents and optionally PA monomers of PHU or PRE-PA or a blend of PRE-PA and PA to ensure that the preparation b contains amine functions from polyamines.

4. The composition of claim 1, obtained by polymerization or covalent bound formation between the constituents of two preparations a and b, wherein the preparation a has at least 1% of glycosaminoglycans, hydrolyzed glycosaminoglycans, glycosamines, or chemically modified glycosaminoglycan, hydrolyzed glycosaminoglycans, glycosamines with CC or with PRE-CC or a blend of those different constituents and chemically modified collagens, elastins, keratins, fibronectins, actins, myosins, laminins, peptides, or a blend of those constituents hydrolyzed, fibrillated or not terminated by CC functions in a blend containing acceptable solvents and optionally CC monomers of PHU or a PRE-CC or a blend of PRE-CC and CC to ensure that the preparation a contains CC functions, and the preparation b contains PA monomers PHU or PRE-PA or a blend of PRE-PA and PA optionally in acceptable solvents to ensure that the preparation b contains amine functions from polyamines.

5. The composition of claim 1, obtained by polymerization or covalent bound formation between the constituents of two preparations a and b, wherein the preparation a contains CC monomers of PHU or PRE-CC of PHU or a blend of PRE-CC and CC optionally in acceptable solvents to ensure that the preparation b contains CC functions and, the preparation b contains chemically modified, glycosaminoglycan, hydrolyzed glycosaminoglycans, glycosamines or a blend of those constituents, terminated by amine functions and at least 1% of collagens, elastins, keratins, fibronectins, actins, myosins, laminins, peptides, hydrolyzed, fibrillated or not, or chemically modified collagens, elastins, keratins, fibronectins, actins, myosins, laminins, peptides, hydrolyzed, fibrillated or not with PA or with PRE-PA or a blend of those constituents in a blend containing acceptable solvents and optionally PA monomers PHU or PRE-PA or a blend of PRE-PA and PA to ensure that the preparation b contains amine functions from PA.

6. The composition of claim 1, wherein the CC monomers are cyclic polycarbonates of cycles of 5 to 8 atoms obtained from polyhydroxylated molecules containing at least three, primary or secondary, non-aromatic, hydroxyl functions, and the PA monomers are primary or secondary PA.

7. The composition of claim 5, wherein the PRE-CC is PHU of 1 to 200,000, CC and PA monomers, terminated by CC monomers, and the PRE-PA is a PHU of 1 to 200,000, CC and PA monomers, terminated by PA monomers.

8. The composition of claim 1, wherein the chemical modification of the glycosaminoglycans, the hydrolysed glycosaminoglycans, the glycosamines of glycosaminoglycans or the blend of the different glycosaminoglycans, hydrolysed glycosaminoglycans, glycosamines of glycosaminoglycans is an esterification, or a deacetylation followed by an esterification and a carbamatation, or a deacetylation followed by a carbamatation with CC or PRE-CC.

9. The composition of claim 1, wherein the first constituent is chemically modified through an amidation with the monomer PA or PRE-PA or a combination of both.

10. The composition of claim 1, wherein the first constituent is chemically modified and is carbamated with the monomer PA or PRE-PA.

11. The composition of claim 1, wherein the CC monomers are cyclic polycarbonates of erythritol, xylitol, arabitol, ribitol, sorbitol, dulcitol, mannitol, maltitol, isomaltitol, lactitol, or polyether polyols and their mixtures.

12. The composition of claim 1, wherein the CC monomers are cyclic polycarbonates of (1,2-dihydroxyethyl), or (2,3-dihydroxypropyl) ether, ester, ketone, amide, phosphate, sulphate, sulphide, disulfide, alkanes, cycloalkanes, alkenes, cycloalkenes, aryls, or heterocycles containing one or more oxygen atom, or aromatic heterocycles containing one or more nitrogen or sulphur atom.

13. The composition of claim 1, wherein the cyclic polycarbonates monomers (CC) are a mixture cyclic polycarbonates of erythritol, xylitol, arabitol, ribitol, sorbitol, dulcitol, mannitol, maltitol, isomaltitol, lactitol, or polyether polyols and their mixtures, or (1,2-dihydroxyethyl), (2,3-dihydroxypropyl) ether, ester, ketone, amide, phosphate, sulphate, sulphide, disulfide, alkanes, cycloalkanes, alkenes, cycloalkenes, aryls, or heterocycles containing one or more oxygen atom, or aromatic heterocycles containing one or more nitrogen or sulphur atom.

14. The composition of claim 1, wherein the constituent (A) is a glycosaminoglycan, a hydrolysed glycosaminoglycan, a glycosamine of glycosaminoglycan, chemically modified or not or a blend of different glycosaminoglycans, hydrolyzed glycosaminoglycans, glycosamines of glycosaminoglycans chemically modified or not taken from the list of including the following substances:
chondroitin sulphates;
hyaluronic acid;
heparan sulphates;
dermatan sulphates;
keratan sulphates; and
aggrecans.

15. The composition of claim 2, wherein the chemical modifications of collagens, elastins, keratins, fibronectins, actins, myosins, laminins, peptides or a blend of those proteins or peptides, hydrolyzed, fibrillated or not are amidation with PA or PRE-PA or a blend of PA and PRE-PA or successive amidation with PA and PRE-PA.

16. The composition of claim 2, wherein the chemically modified collagens, elastins, keratins, fibronectins, actins, myosins, laminins, peptides or a blend of those proteins or peptides, hydrolyzed, fibrillated or not is carbamated with the CC monomer or Pre-polymer PRE-CC.

17. The composition of claim 2, which is further carbamated successively with PA and CC to obtain PA or CC terminated PHU chemically grafted on collagens, elastins, keratins, fibronectins, actins, myosins, laminins, peptides or a blend of those proteins or peptides, hydrolyzed, fibrillated or not.

18. The composition of claim 1, wherein the primary and secondary PA monomers are primary or secondary polyamines of ether, ester, ketone, amide, phosphate, sulphate, sulphide, disulfide, alkanes, cycloalkanes, alkenes, cycloalkenes, aryls, substituted or not with hydroxyl functions; or primary or secondary polyamines and primary or secondary polyalkylamines of heterocycles containing one or more oxygen, nitrogen or sulphur atom, substituted or not with hydroxyl functions; or polyetheramines simple or mixed of ethylene glycol and propylene glycol; or a mixture of those compounds.

19. The composition of claim 1, wherein the ratio of the number of non polymerized, or covalently bound carbonate cyclic functions from CC monomers, PRE-CC and chemically modified first and second constituents, and the number of non polymerized, or covalently bound primary and secondary amine functions from PA monomers, the PRE-PA and the chemically modified first and second constituents are between 50 and 0.02.

20. The composition of claim 1, wherein a catalyst or a blend of catalyst taken from the ionic or covalent form of Li, Na, K, Mg, Zn, B and Al or an Infrared photonic source is used to control the polymerization or covalent bounds formation between cyclic carbonates and primary or secondary amines functions.

21. The composition of claim 1 for the substitution or the reconstruction of connective, epithelial, nervous, muscular, bones, cartilaginous, or dermal, animal or human extra cellular matrix for which the ratio of the number of non polymerized, or covalently bound carbonate cyclic functions from CC monomers, PRE-CC and chemically modified first and second constituents, and the number of non polymerized, or covalently bound primary and secondary amine functions from PA monomers, the PRE-PA and the chemically modified first and second constituents are between 2 and 0.5.

22. The composition of claim 1 for coating the surfaces of foreign materials implanted in living organisms for permanent or transitory periods.

23. The composition of claim 1 as carrier, modifier or protector of living cells, biological and pharmacological materials and substances.

24. A composition comprising a first, second and third constituents, wherein
the first constituent is a glycosaminoglycan, a hydrolyzed glycosaminoglycan, a glycosamine, chemically modified or not or a blend of different glycosaminoglycans, hydrolysed glycosaminoglycans, glycosamines, chemically modified or not;
the second constituent is a protein, a peptide or a blend of different proteins or peptides; and
the third constituent is a polyhydroxyurethane (PHU) which is obtained by the covalent coupling of bis or poly cyclic carbonates (CC) and di or polyamines (PA) molecules,
wherein the ratio of the number of non polymerized, or covalently bound carbonate cyclic functions from CC monomers, PRE-CC and chemically modified first and second constituents, and the number of non polymerized, or covalently bound primary and secondary amine functions from PA monomers, the PRE-PA and the chemically modified first and second constituents are between 50 and 0.02.

* * * * *